United States Patent
De Kruif et al.

(10) Patent No.: US 6,831,741 B1
(45) Date of Patent: Dec. 14, 2004

(54) ARRANGEMENT AND METHOD TO APPLY DIFFUSING WAVE SPECTROSCOPY TO MEASURE THE PROPERTIES OF MULTI-PHASE SYSTEMS, AS WELL AS THE CHANGES THEREIN

(75) Inventors: Cornelis Gijsbertus De Kruif, Woudenberg (NL); Erik Ten Grotenhuis, Ede (NL); David Allan Weitz, New Hope, PA (US); Goro Nishimura, Sapporo (JP); Arjun Gaurang Yodh, Merion, PA (US)

(73) Assignee: Stichting Nederlands Instituut voor Zuivelonderzoek (NIZO), Ba Ede (NL)

( * ) Notice: Subject to any disclaimer, the term of this patent is extended or adjusted under 35 U.S.C. 154(b) by 0 days.

(21) Appl. No.: 09/647,684

(22) PCT Filed: Apr. 6, 1999

(86) PCT No.: PCT/NL99/00201

§ 371 (c)(1),
(2), (4) Date: Aug. 22, 2001

(87) PCT Pub. No.: WO99/51954

PCT Pub. Date: Oct. 14, 1999

(30) Foreign Application Priority Data

Apr. 2, 1998 (EP) .......................................... 98201042

(51) Int. Cl.[7] .............................................. G01N 21/00
(52) U.S. Cl. ..................................... 356/338; 356/337
(58) Field of Search ................................ 356/300, 301, 356/337, 338, 343

(56) References Cited

U.S. PATENT DOCUMENTS

| | | | | |
|---|---|---|---|---|
| 4,768,879 A | * | 9/1988 | McLachlan et al. | 356/301 |
| 4,969,741 A | * | 11/1990 | Kennedy et al. | 356/338 |
| 5,172,193 A | * | 12/1992 | Payne et al. | 356/445 |
| 5,434,667 A | * | 7/1995 | Hutchins et al. | 356/338 |
| 5,502,561 A | * | 3/1996 | Hutchins et al. | 356/336 |
| 6,016,195 A | * | 1/2000 | Peters | 356/342 |
| 6,076,010 A | * | 6/2000 | Boas et al. | 600/477 |
| 6,519,032 B1 | * | 2/2003 | Kuebler et al. | 356/337 |

FOREIGN PATENT DOCUMENTS

EP 0 359 681 * 3/1990

OTHER PUBLICATIONS

S.E. Harding: "Laser Light Scattering in Biochemistry, Chapter 15 (David S Horne; Dynamic Light Scattering Studies of Concentrated Casein Micelle Suspensions)" Chemical Abstracts + Indexes.*

* cited by examiner

Primary Examiner—Rodney Fuller
(74) Attorney, Agent, or Firm—Bachman & LaPointe, P.C.

(57) ABSTRACT

Arrangement for measuring physico-chemical properties of liquid, such as solutions, dispersions and emulsions. The arrangement comprises a light source for producing and emitting light in the liquid, a detector for detecting said light after being scattered by said liquid, processing means arranged for receiving an output signal from said detector. The processing means is further arranged to calculate a maximum value of the mean square displacement $<\Delta r_m^2>$ from the autocorrelation function $g^{(2)}$ as a function of time and the value of the property from said calculated maximum value of the mean square displacement $<\Delta r_m^2>$.

21 Claims, 11 Drawing Sheets

ARRANGEMENT AND METHOD TO APPLY DIFFUSING WAVE SPECTROSCOPY TO MEASURE THE PROPERTIES OF MULTI-PHASE SYSTEMS, AS WELL AS THE CHANGES THEREIN

BACKGROUND OF THE INVENTION

The present invention relates to an arrangement for measuring the properties of multi-phase systems as well as the changes therein, such as changing interactions between particles in a solution. In particular, the invention relates to such an arrangement for use with multi-phase systems in which at least one of the phases is a liquid phase or fluid, such as gels, lattices, suspensions or emulsions.

The arrangement of the invention comprises a light source for producing a light beam. It is possible to use at least one source fibre having a first end arranged for receiving said laser beam and a second end arranged for emitting light in a multi-phase system, or to point the light directly into the multi-phase system. At least one detector fibre, arranged for detecting said light after being scattered by said multi-phase system, processing means arranged for receiving an output signal from said at least one detector fibre and for calculating predetermined parameters with respect to said multi-phase system.

Such an arrangement is known from D. S. Horne, Dynamic Light Scattering Studies of Concentrated Casein Micelle Suspensions, Chapter 15 in S. E. Hardings, e.a. Laser Light Scattering in Biochemistry, 1992.

The Diffusing Wave Spectroscopy (DWS) arrangement described by Horne, comprises a bifurcated optical fibre bundle as light guide. Half the fibres are connected to a randomly polarized He—Ne laser. The other half of the fibres is connected to a photomultiplier. The bundle of fibres is distributed randomly over the face of a common leg. In use, the non-connected ends of the fibres are dipped into a scattering multi-phase system, e.g. milk or a milk derived medium/solution. Those fibres which are connected to the laser emit laser light into the multi-phase system. Light backscattered by the multi-phase system is detected by the fibres connected to the photomultiplier. Masking by a slit and a pinhole may ensure that light from only a small area impinges on the detector.

With such an arrangement, intensity correlation functions can be measured. Examples of such functions are presented for 330 nm polystyrene latex and undiluted skim milk. Moreover, Horne shows that relaxation time as a function of casein micelle volume fraction in reconstituted milk can be measured, Horne also shows that the relaxation time changes due to curd formation. Thus, the transition from fluid to gel can be detected. One of Horne's conclusions is that: "It therefore appears that observation of DWS behaviour in these gelling systems, by virtue of its measurement of relaxation in the system, must eventually reflect changes in visco-elastic properties". However, Horne does not indicate how visco-elastic properties may be quantitatively derived from DWS measurements.

Moreover, the measurements described by Horne can not easily be made quantitative because these measurements are made with a randomly distributed bundle of incoming and outgoing optical fibres.

A. C. M. van Hooydonk, e.a., Control and Determination of the Curd-setting during Cheesemaking, Bulletin of the International Dairy Federation (1988) (No. 255), pp. 2–10, observe that a lot of scientific research has been devoted to rennet-induced coagulation of milk. However, up to now no quantitative measurement of gel formation and the subsequent synersis of the curd is available. The optimum coagulum firmness must be determined on-line for cutting to obtain maximum cheese yield and cheese quality. Hooydonk e.a. note: "Up to now most cheesemakers judge the optimum cutting time by the "feel" of the curd and . . . with amazing accuracy". Moreover, they note that although many instruments have been developed to carry out this task automatically, none of them have been widely accepted. The so-called "Gelograph" is considered as a standard instrument for measuring the gelation of cheesemilk at low gel strength. However, due to ongoing automation and increase of scale of cheesemaking plants there is a strong interest in automatic methods for monitoring the process of curd-setting.

In the U.S. Pat. No. 4,975,237 a dynamic light scattering apparatus is disclosed, comprising a laser as light source, optically coupled to a light scattering sample via a first optical fibre and a first lens. The lens produces a beam waist in a sample and scattered light is collected by a receive lens and a receive fibre. A photodetector detects light transmitted by the receive fibre and converts it in an electrical signal. The photodetector is connected to a correlator and computer. This correlater is not used for quantitative measurements of characteristics of the sample.

A primary object of the present invention is to provide an apparatus with which the properties of liquids, such as solutions, dispersions and emulsions can be measured and to relate physico-chemical properties to light scattering measurement in liquids.

SUMMARY OF THE INVENTION

For the purposes of the invention, the term "liquids" comprises both heterogeneous systems which contain two distinct phases, such as a liquid phase and a suspended solid phase, two immiscible liquid phases, or an emulsified (liquid) phase in a liquid phase, as well as more homogeneous systems which are subject to phase changes, phase transitions or phase formation, such as systems in which gel formation, coagulation, aggregation or changes in viscosity can occur.

These homogenous or heterogenous systems can comprise organic, inorganic as well as biological media or components, aqueous systems or solutions, or systems of a mixed organic/inorganic and/or biological nature. In a particular embodiment, the multi-phase system is milk or a milk derived medium/solution, for instance as used in cheese-making.

A further object of the present invention is to provide a method which can be carried out by an apparatus according to the invention and which is able to provide physico-chemical properties of such liquids by means of diffusing wave spectroscopy. Such a method may be related to monitoring the renneting of cheesemilk during cheese-making, but is not restricted thereto.

Thus, the arrangement according to a first aspect of the present invention as defined above is characterized in that a processing means is arranged to calculate a maximum value of the mean square displacement $<\Delta r_m^2>$ from the autocorrelation function $g^{(2)}$ as a function of time and the value of the physico-chemical property from said calculated maximum value of the mean square displacement $<\Delta r_m^2>$.

In an embodiment the physico-chemical property is the gel-strength G' which is calculated using the following equation:

$$G' \approx \frac{k_B T}{\xi \left\langle \Delta r_m^2 \right\rangle}$$

in which, $k_b \cdot T$ = thermal energy of particles in the gel;

$\xi$ = size of a cluster in the gel.

The arrangement according to a second aspect of present invention is characterized in that a processing means is arranged to determine the half decay time as a function of time of the autocorrelation function and to determine the value of the physico-chemical property using a predetermined relation between the half decay time and the autocorrelation function. This value may be the gelstrength.

A further difference between the arrangement according to the invention and the Horne arrangement is the configuration of the optical fibres. Whereas the fibres in the Horne arrangement are distributed randomly and the mutual distances between the fibres is unknown, in the arrangement according to the invention the mutual distances between the detector fibres are predetermined. In order to facilitate the calculations the detector fibres are, preferably, single-mode fibres suitable for one specific monochromatic wavelength. The fibres are preferably set up in the so-called "backscattering geometry", which makes it possible to quantify the autocorrelation function that is measured. They may have the shape of a dipstick, so they can be easily stuck into any kind of liquid.

The advantage of DWS in respect to the gelograph is that changing interactions between the (droplets, bubbles or particles of the) phrases can be measured. In the case of renneting of cheesemilk the effects of the addition of rennet can be observed in a much earlier stage of the process. The method is non-destructive, because its working principle is not based on mechanical principles, but on the scattering of monochromatic light that does not damage the liquid.

Furthermore, the DWS can be used to do local measurements, which also makes it possible to probe inhomogeneities in samples. The volume that is probed by one pair of source fibre and detector fibres ranges from 1 nl to 1 l or more and can be located in an infinitely large volume. It depends on the distance between the source fibre and detector fibres.

In one embodiment of the arrangement according to the invention a source fibre and the at least one detector fibre are immersed in a milk with an addition of a rennet.

In order to automatically cut cheesemilk at the proper gel-strength, in a further embodiment the arrangement comprises a cutting machine coupled to the processing means, wherein the processing means are arranged to compare the gelstrength with a reference gelstrength, and to activate the cutting machine upon the gelstrength reaching the reference gelstrenth for cutting the gel.

Moreover, a third aspect of the invention is directed to a method for measuring the physico-chemical properties of liquids such as solutions, dispersions and emulsions, comprising the steps of:

producing a light beam (2)

emitting light in a liquid (7);

detecting said light after being scattered by said liquid (7);

converting the detected light in an electrical signal;

transmitting said electrical signal to processing means;

calculating the autocorrelation function $g^{(2)}$ in the time- or the frequency domain of said electrical signal characterized in that a maximum value of the mean square displacement $\langle \Delta r_m^2 \rangle$ is calculated from the autocorrelation function $g^{(2)}(\tau)$, or from $g^{(2)}(\nu)$ in a similar way, as a function of time and the value of said property is calculated from said calculated maximum value of the mean square displacement $\langle \Delta r_m^2 \rangle$. The value may be the gelstrength which is calculated using the following equation:

$$G' \approx \frac{k_B T}{\xi \left\langle \Delta r_m^2 \right\rangle}$$

in which, $k_b \cdot T$ = thermal energy of particles in the gel;

$\xi$ = size of a cluster in the gel.

A fourth aspect of the invention is directed to a method for measuring physico-chemical properties of liquids such as solutions, dispersions and emulsions, comprising the steps of:

producing a light beam (2)

emitting light in a liquid (7);

detecting said light after being scattered by said liquid (7);

converting the detected light in an electrical signal;

transmitting said electrical signal to processing means;

calculating the autocorrelation function $g^{(2)}$ of said electrical signal, characterized in that the half decay time is calculated as a function of time of the autocorrelation function and the value of said property is determined using a predetermined relation between the half decay time and the autocorrelation function. The value may be the gelstrength.

BRIEF DESCRIPTION OF THE DRAWINGS

The invention will be explained in detail with reference to some drawings which are intended to illustrate the present invention and not to limit its scope.

DETAILED DESCRIPTION

Figure 1:
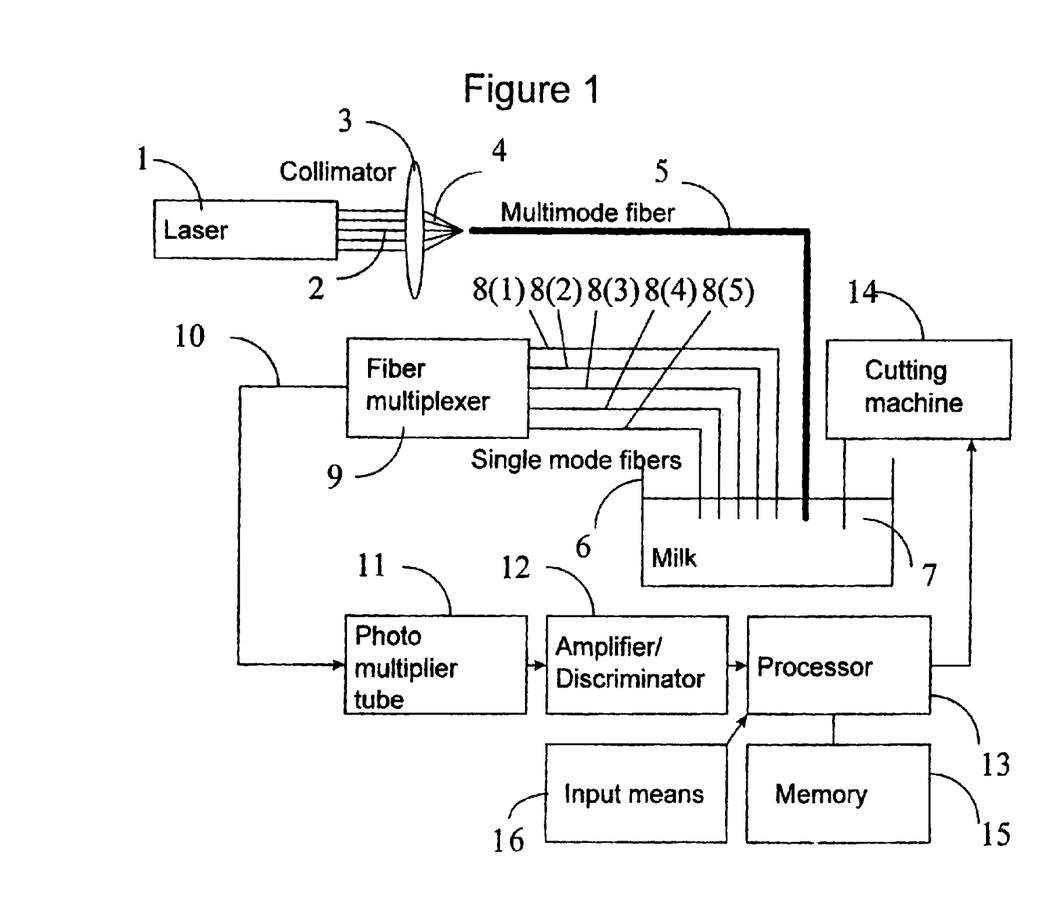
FIG. 1 shows a schematical block diagram of an arrangement according to the invention.

FIG. 1 shows a possible embodiment of a diffusing wave spectroscopy arrangement according to the invention. The arrangement shown comprises a laser 1, which may be an Ar+ laser with a wavelength of 514 nanometre. The laser 1 generates a laser beam 2 which is directed to a collimator 3 which produces a collimated laser beam 4 directed to a multimode fibre 5. The laser light may be coupled into the multimode fibre 5 by means of a fibre coupler F220SMA-S, Thorlabs, mounted on a tilting stage. The multimode fibre 5 may be a fibre FG-50-GLA, Thorlabs, having a core diameter of 50 micrometer. In use, the multimode fibre 5 is immersed with one end in a multi phase system/solution 7, e.g. milk, in a container 6.

In the arrangement shown in FIG. 1, there are shown five detector fibres 8(1), . . . , 8(5), located at predetermined distances from the multimode fibre 5. However, the number of detector fibres may be 1 or more. The detector fibres are preferably single mode fibres. They are connected to a fibre multiplexer 9 which may be a Dicon fibre multiplexer.

The output of the fibre multiplexer 9 is connected via a connection 10 to a photomultiplier tube 11, e.g. a HC-120PMT, Hamamatsu, which is in turn connected to an amplifier/discriminator 12. The amplifier/discriminator 12 is connected to a processor 13 which comprises a computer mounted correlator board, e.g., a Brookhaven Instruments 9000. Data acquisition and analysis will be carried out by processor 13. The processor 13 is connected to a memory 15 and input means like a keyboard, a mouse, etc.

In one embodiment the processor 13 is connected to a cutting machine 14 for cutting gelated milk when it has reached the proper gelstrength in a cheese making process.

In use, the multimode fibre 5 emits laser light into the multi-phase system 7. The laser light is multiple scattered by the multi-phase system and the multiple scattered laser light will be detected by the detector fibres 8 (1), . . . , 8 (5). These detector fibres may be single mode fibres FS-VS-2614, Thorlabs. With the fibre multiplexer 9 one channel picking up the signal of one of the detector fibres 8 (1), . . . , can be selected for measurement of a correlation function.

In one experiment the multi-phase system 7 was fresh skim milk. Whereas in another experiment the multi-phase system 7 was whole milk. Both were obtained from Wawa supermarkets.

Skim milk did contain a negligible amount of fat, whole milk contained 33 g/l fat. The milk was poured in container 6 (6.6 cm×12.0 cm×11.0 cm) and brought to a temperature of 30° C. by putting the container in a water batch (not shown). The temperature of the milk was controlled by replacing cold water with hot water at regular intervals. In this way, the temperature could be kept within 2° C. from 30° C.

Rennet was added at a usual concentration of 20 ml per 100 l (0.02%) of milk. To skim milk higher concentrations of 0.04% and 0.08% were also added. In the first experiments autocorrelation functions and intensities of detected, backscattered laser light were measured for each channel during 60 s at relatively large intervals. Later, the correlation functions and the intensities on the channel, which has a source detector separation of 4.9 mm between the end of multimode fibre 5 and the end of detector fibre 8 (1) immersed in multi-phase system 7, was measured in 30 s in 60 s intervals during a period of several hours. The fibre multiplexer 9 was left in the setup, but did not have a function in these latter measurements.

Before showing some measurement results, first, some theory will be given.

The expression for the intensity in an indefinite system is:

$$I(\rho) = \frac{A\mu'_s}{\rho} \exp\left(-\sqrt{3\mu_a \mu'_s}\, \rho\right) \quad (1)$$

wherein A is a constant, depending on e.g. the laser input power and the coupling efficiencies of the fibres, $\mu_a$ is the absorption coefficient and $\rho$ is the source-detector separation. $\mu'_e$ is the reciprocal of the mean free path, $1^*$. The electric field correlation function $g^{(1)}(\tau)(=<E_s^*(0)E_s(\tau)>/<E_s^2>)$ for the backscattering geometry is given by:

$$g^{(1)}(\tau) = \exp\left\{-\rho\mu'_s \sqrt{\langle \Delta r^2(\tau)\rangle q_0^2 + 3\frac{\mu_a}{\mu'_s}}\right\} \quad (2)$$

wherein $\Delta r^2(\tau)$ is the mean square displacement; $q_0$ is the wave vector related to the wave length and $\tau$ is the measuring time between two successive measuring points.

Since the autocorrelation function $g^{(2)}(\tau)$ of the intensity I ($g^{(2)}(\tau)=<I(o)\cdot I(\tau)>/<I^2(o)>$) is given by the Siegert relation.

$$g^{(2)}(\tau)=1+\beta|g^{(1)}(\tau)|^2 \quad (3)$$

herein $\beta$ is a constant related to the arrangement used, the autocorrelation function $g^{(2)}(\tau)$ can be calculated. In the experiments the baseline at large $\tau$, where $g^{(1)}(\tau)=0$, is measured and used to calculate $g^{(2)}(\tau)$. The factor $\beta$, which should be equal to 0.5 because a single mode fibre 8(1), . . . is used, was estimated from the behaviour of $g^{(2)}(\tau)$ for short correlation times. Finally, the base line was subtracted from the data and the data were normalized for $\beta$, giving $(g^{(2)}(\tau)-1)/\beta$, which is equal to $|g^{(1)}(\tau)|^2$.

For Brownian motion of particles, the mean square displacement can be written as $<\Delta r^2>=6$ D$\tau$, with D the diffusion constant. In this case ln $(g^{(1)}(\tau))/\rho \alpha \sqrt{\tau}$, and the experimental data should form one common line in a graphical representation.

Figure 2:
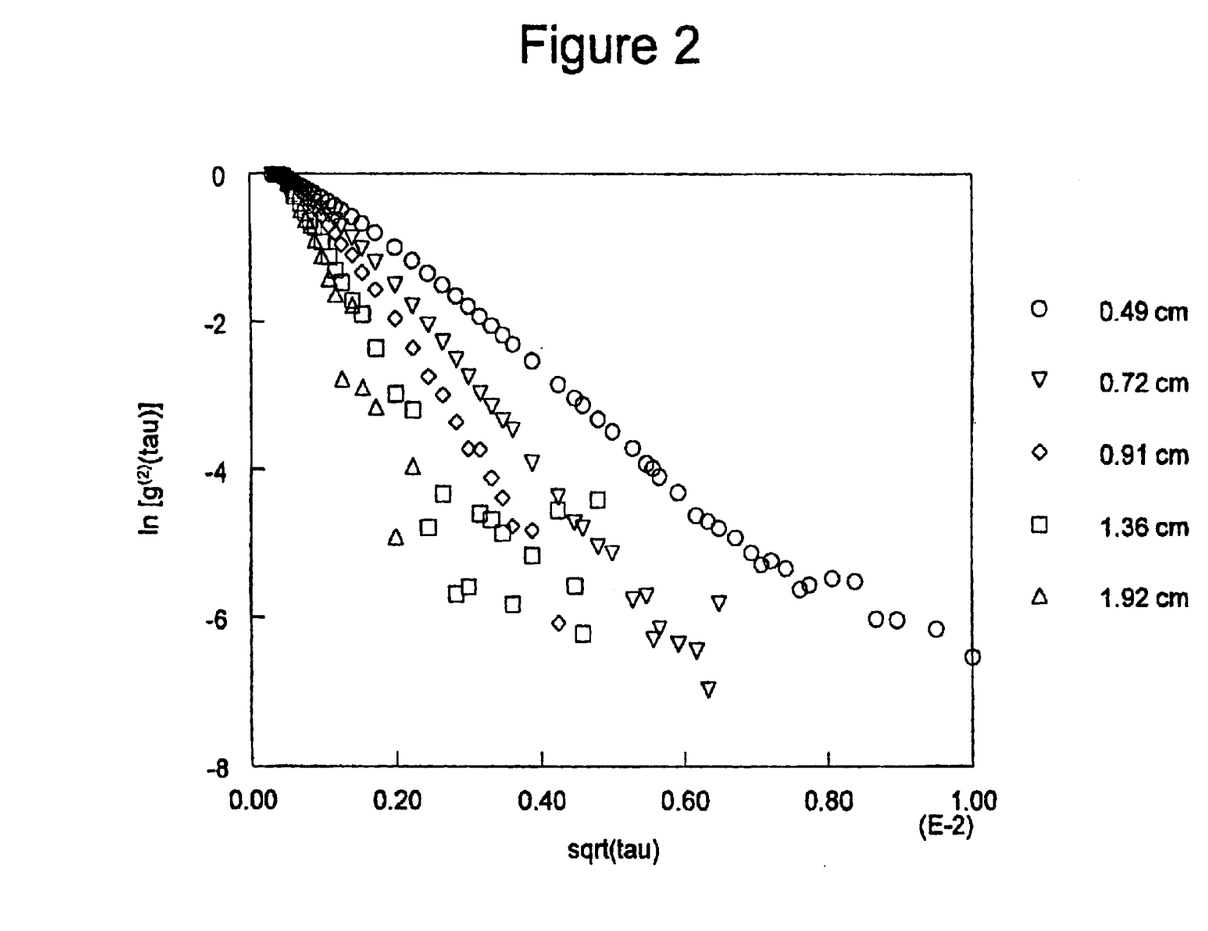
FIG. 2 shows autocorrelation functions for different distances between the source fibre and the detector fibres.
Figure 3:
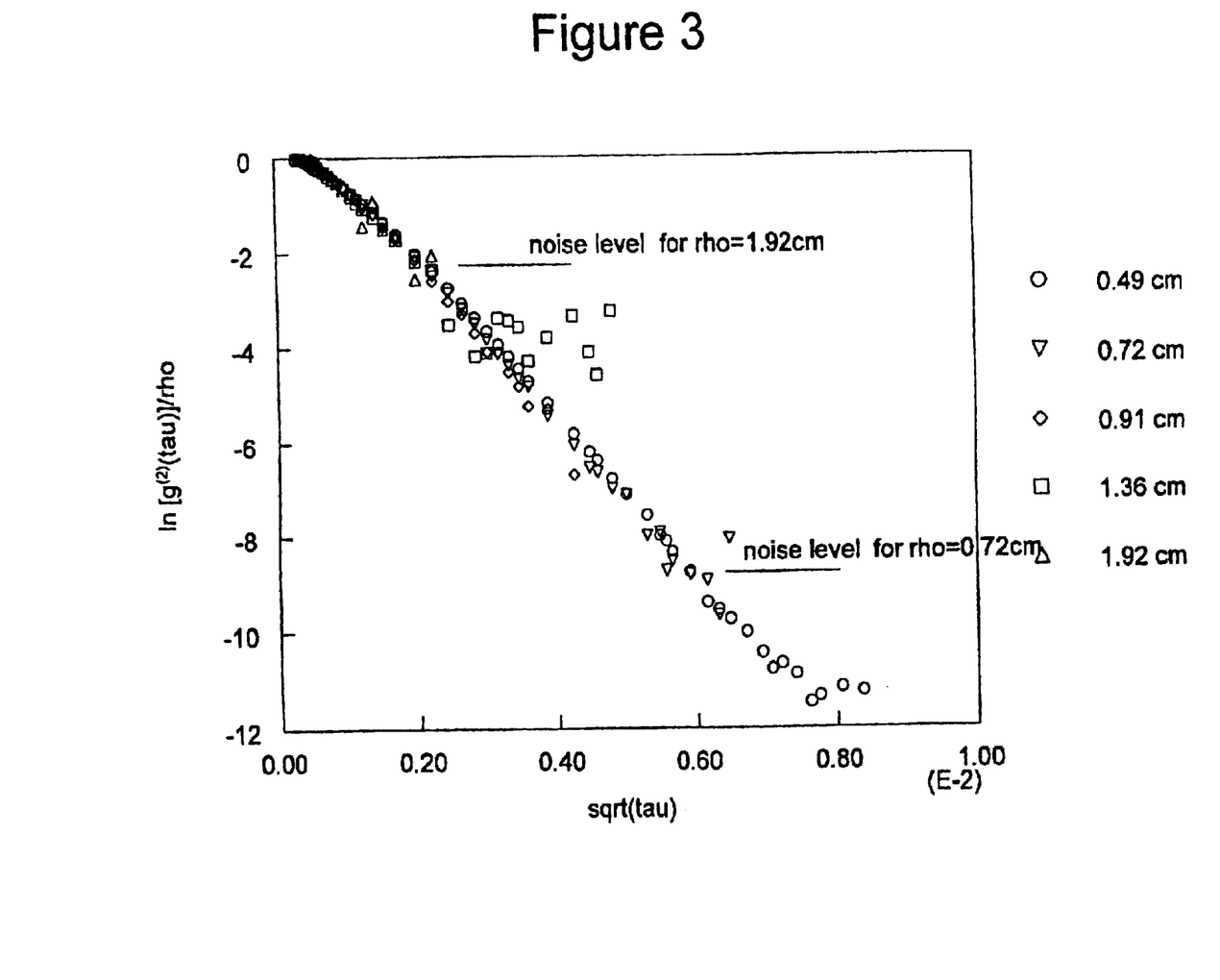
FIG. 3 shows the same data as FIG. 2 but normalized for the distances between the source fibre and the detector fibres.

FIGS. 2 and 3, respectively, show ln($g^{(2)}(\tau)$) and ln($g^{(2)}(\tau))/\rho$, respectively, as a function of $\sqrt{\tau}$ as measured by five fibres (8(1), . . . 8(5)) in skim milk, located at different distances from the source fibre 5 as specified in the righthand portions of FIGS. 2 and 3.

The laser output used for the first experiments was about 300 mW. ln($g^{(2)}(\tau)$) vs $\sqrt{\tau}$ will give a straight line for the Brownian behaviour. The datapoints in the ln($g^{(2)}(\tau))/\rho$ vs $\sqrt{\tau}$ curves are all on the same line, as predicted by the theory (FIG. 3), until $g^{(2)}(\tau)$ reaches the noise level. This is most obvious for the channel with the largest source-detector separation $\rho=1.92$ cm.

Figure 4:
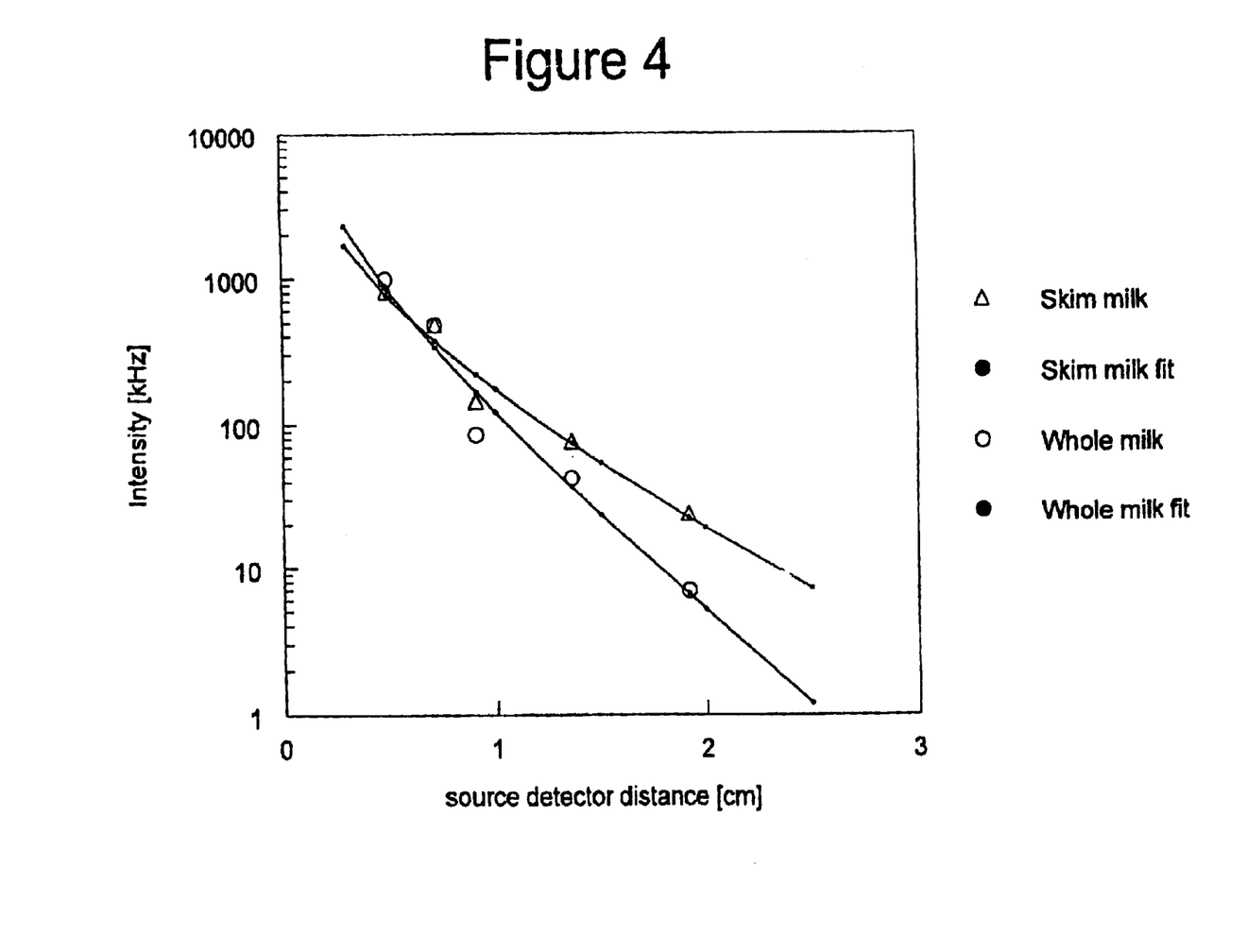
FIG. 4 shows intensity profiles for different types of milk, as a function of source detector distance.

The intensity dependence on the source-detector separation $\rho$ is given in FIG. 4. It was assumed that the fibre/multiplexer couplings all had approximately the same efficiency. The lines are a best fit, with a and $\mu_a'$ as variables. $\mu_a$ is fixed at a value of 0.03 cm$^{-1}$. For A and $\mu_a'$, respectively, we find 31 and 25.7 cm$^{-1}$, respectively, in skim milk and 21 and 67.7 cm$^{-1}$, respectively, in whole milk. This means that the mean free path $1^*$ in skim milk is 0.39 mm and 0.15 mm in whole milk. This is caused by scattering of the fat globules in whole milk.

Figure 5:
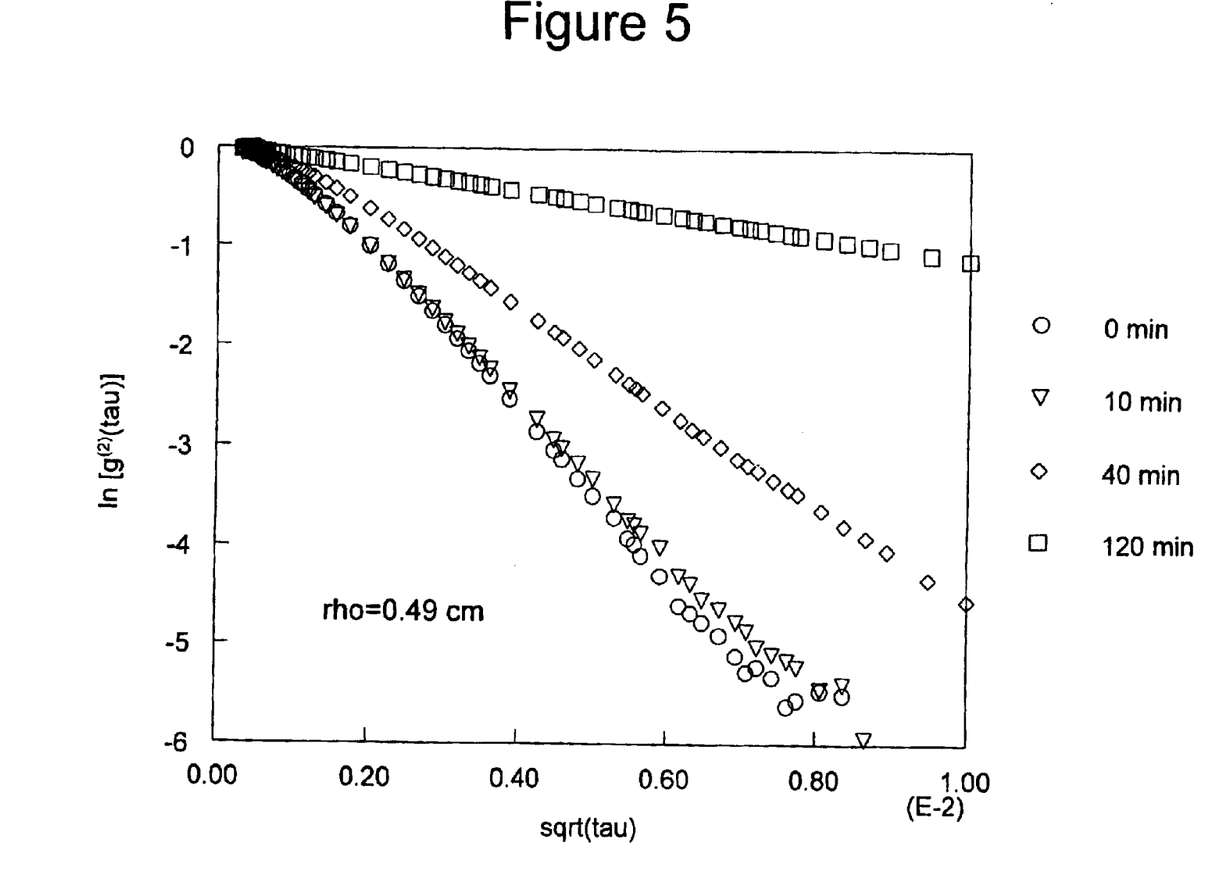
FIG. 5 shows autorcorrelation functions at different times after the addition of rennet to milk for a source detector distance of 4.9 mm.
Figure 6:
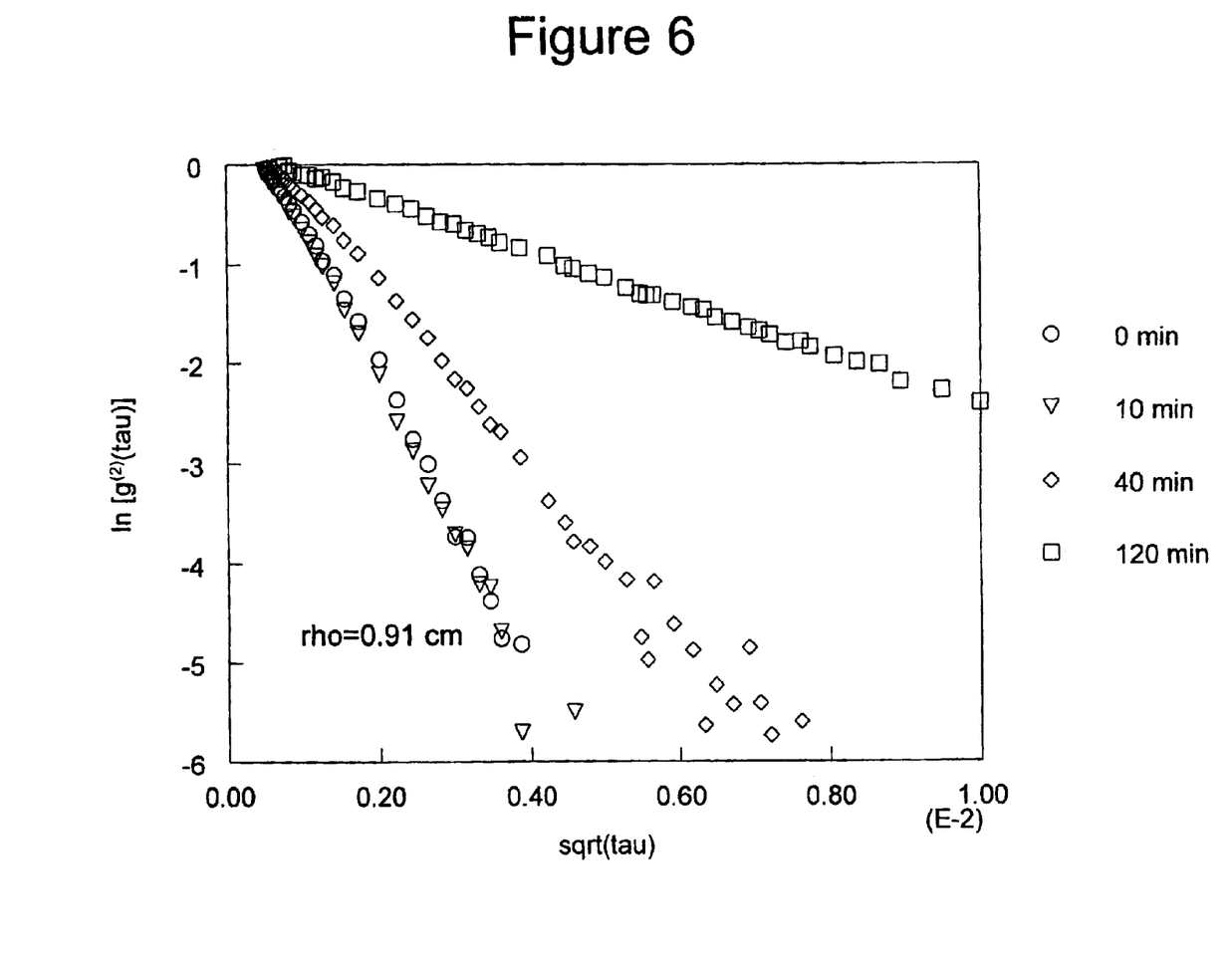
FIG. 6 shows the same data as FIG. 5 but for a source detector distance of 9 mm.

The time-dependence of the correlation functions was followed after the addition of rennet (0.02%) at time 0. The correlation functions were recorded at t<0 (i.e. before addition of rennet), t=10 min. t=40 min. and t=120 min. FIGS. 5 and 6 give the time-dependence of the correlation functions for skim milk measured on the channel where $\rho=4.9$ mm and where ρ=9.1 mm, respectively. These figures show typical correlation functions $\ln(g^{(2)}(\tau), t)$ for milk at t=0 and t=10 min, during the gel formation at t=40 min, and after the gel has formed at t=120 min.

The correlation functions were also measured during 30 s at 1 min intervals to gain more insight in their development in time. Since the change of the correlation functions during gelling seemed to proceed similarly for all source-detector distances between 5 and 19 mm, only the correlation functions for the nearest channel (ρ=4.9 mm) were measured. The power output of the laser 1 was turned down to about 30 mW. The resulting count rate was in the order of 100 kHz. The change in the correlation functions $g^{(2)}(\tau)$ can be expressed in terms of the half decay time, i.e. the time it takes the correlation function $g^{(2)}(\tau)$ to drop to half of its original value. These measurements were performed for skim milk with rennet concentrations of 0.02%, 0.04%, and 0.08%, and for whole milk with a rennet concentration of 0.02%.

Figure 7:
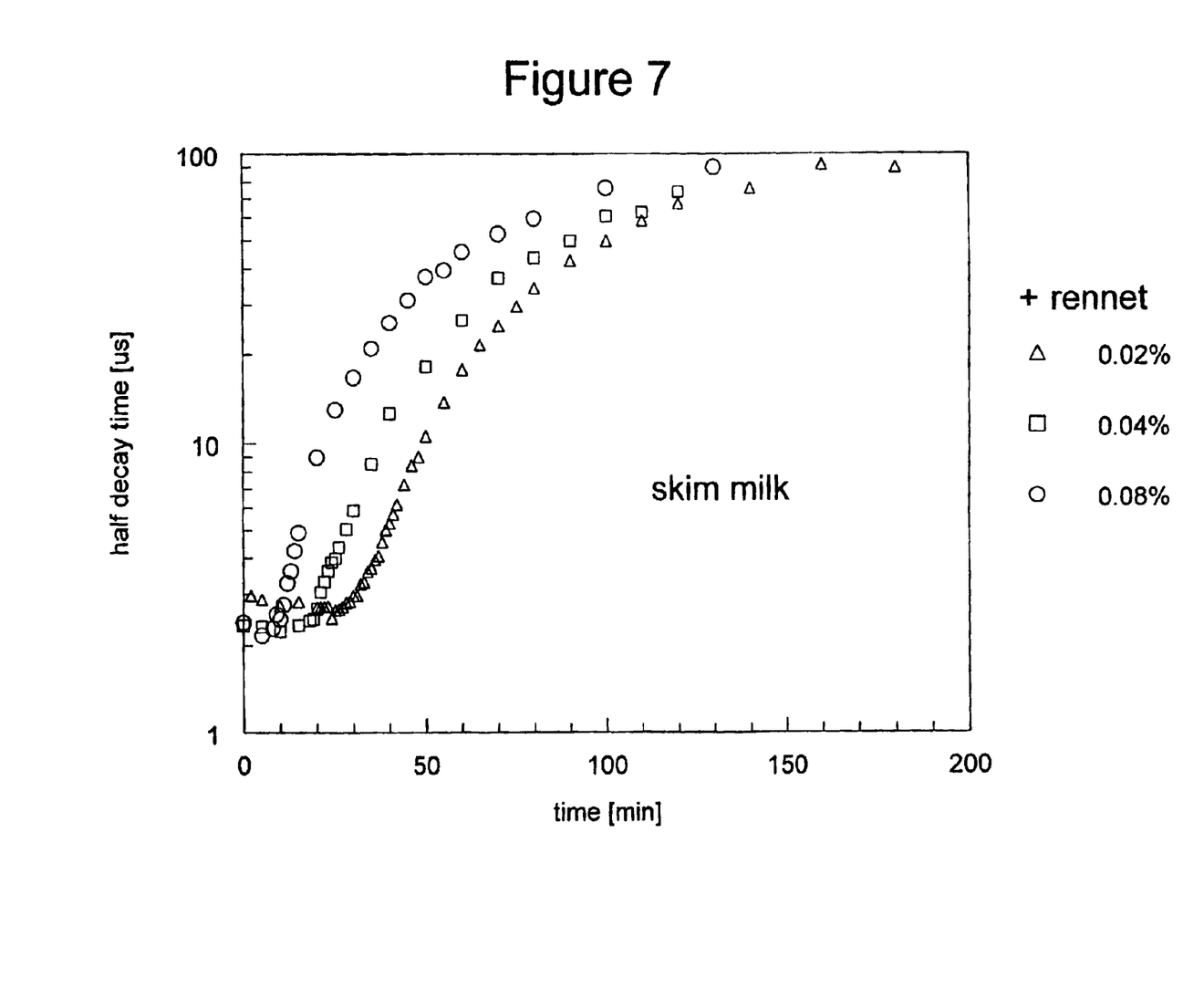
FIG. 7 shows half decay times for different additions of rennet to skim milk as a function of time after the addition of the rennet.
Figure 8:
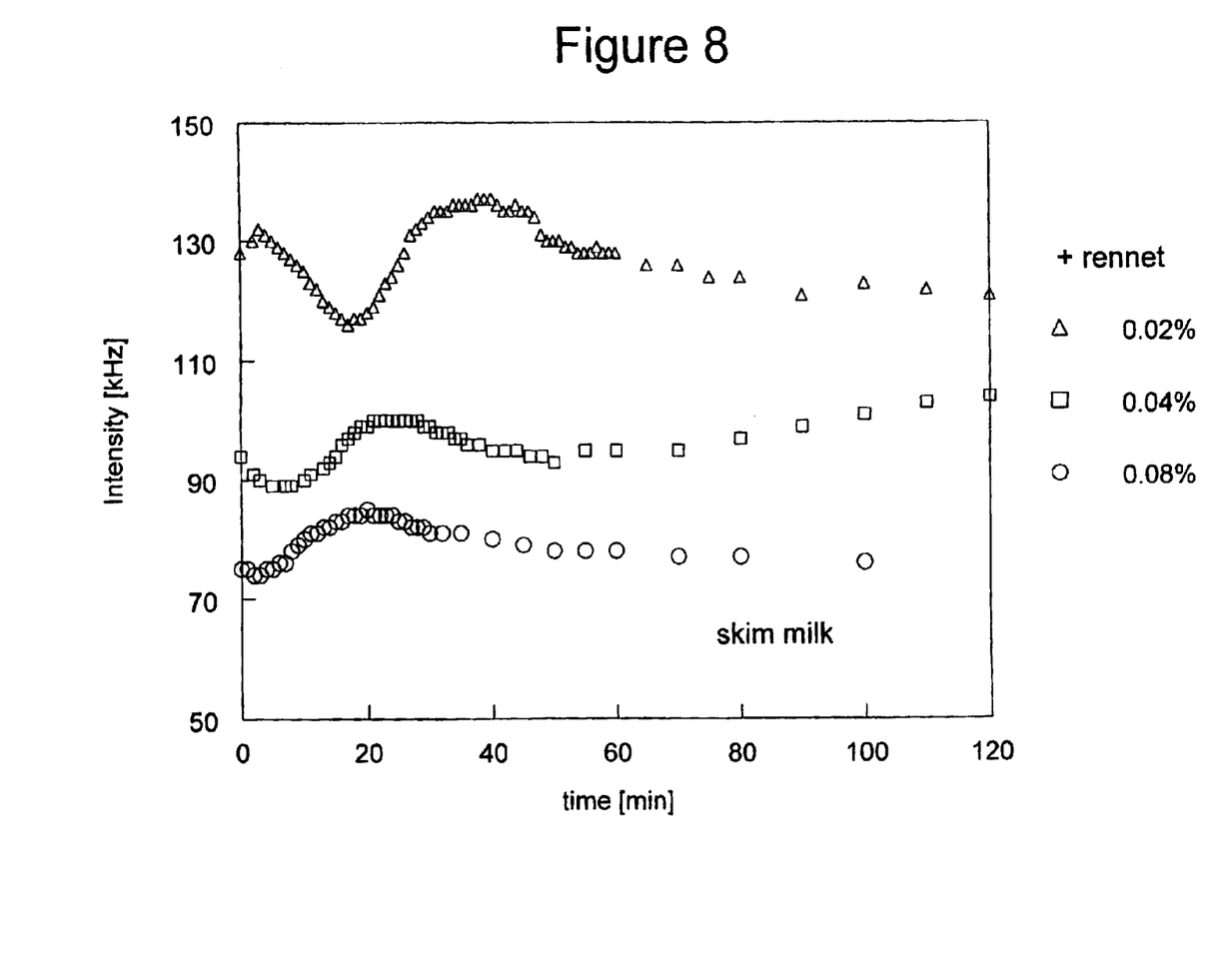
FIG. 8 shows intensity profiles for different additions of rennet to skim milk as a function of time after the addition of the rennet.

The change in the half decay times is shown in FIG. 7 in a log-linear graph. When the rennet concentration is increased the gel formation starts sooner, as expected. The half decay time increases from approximately 2.5 μs for milk to 100 μs for the gel. Before the gel formation starts, i.e. in the period that aggregates are formed, the half decay time decreases slightly. In this same period the intensity profile has a maximum as shown in FIG. 8, that shows the intensity as a function of time in skim milk with different rennet concentrations.

Figure 9:
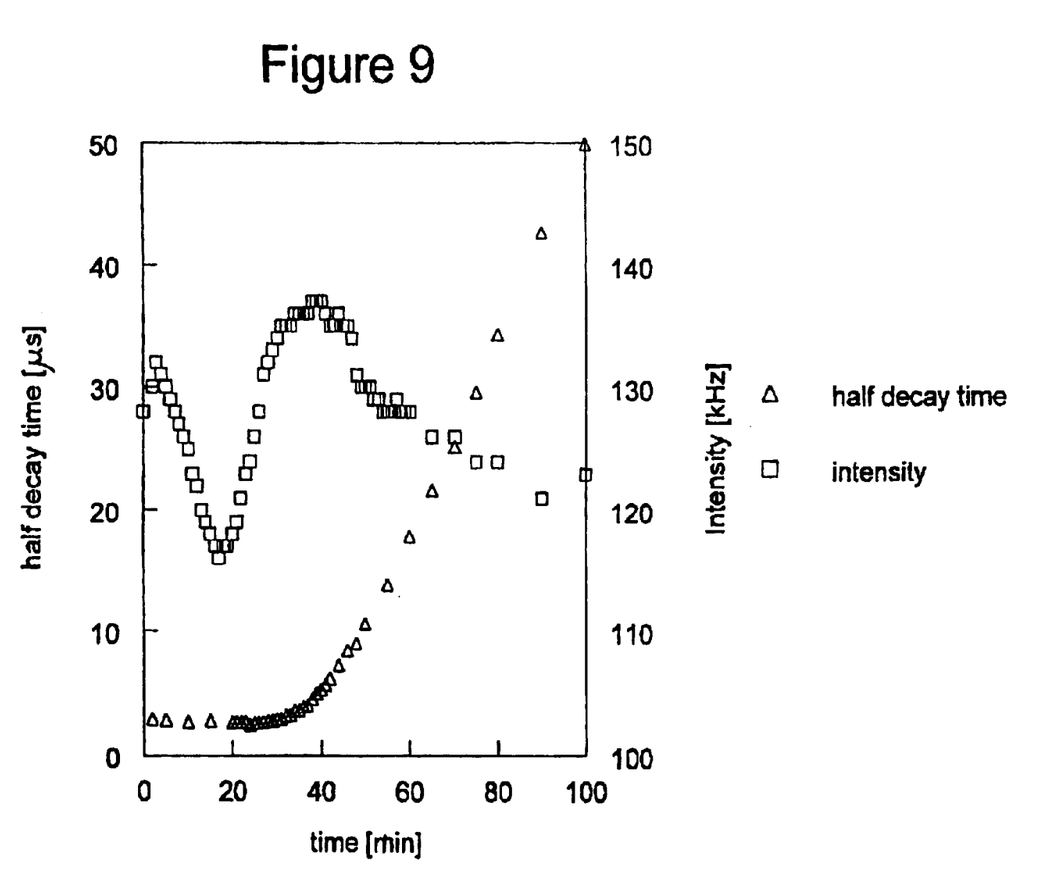
FIG. 9 compares the time dependency of the half decay time and the intensity profile for an addition of 0.02% rennet to skim milk.

For a better comparison both the half decay time and the intensity in skim milk with 0.02% rennet added are given in FIG. 9. The gel formation was checked visually and started approximately at t=40 min when 0.02% rennet was added.

Figure 10:
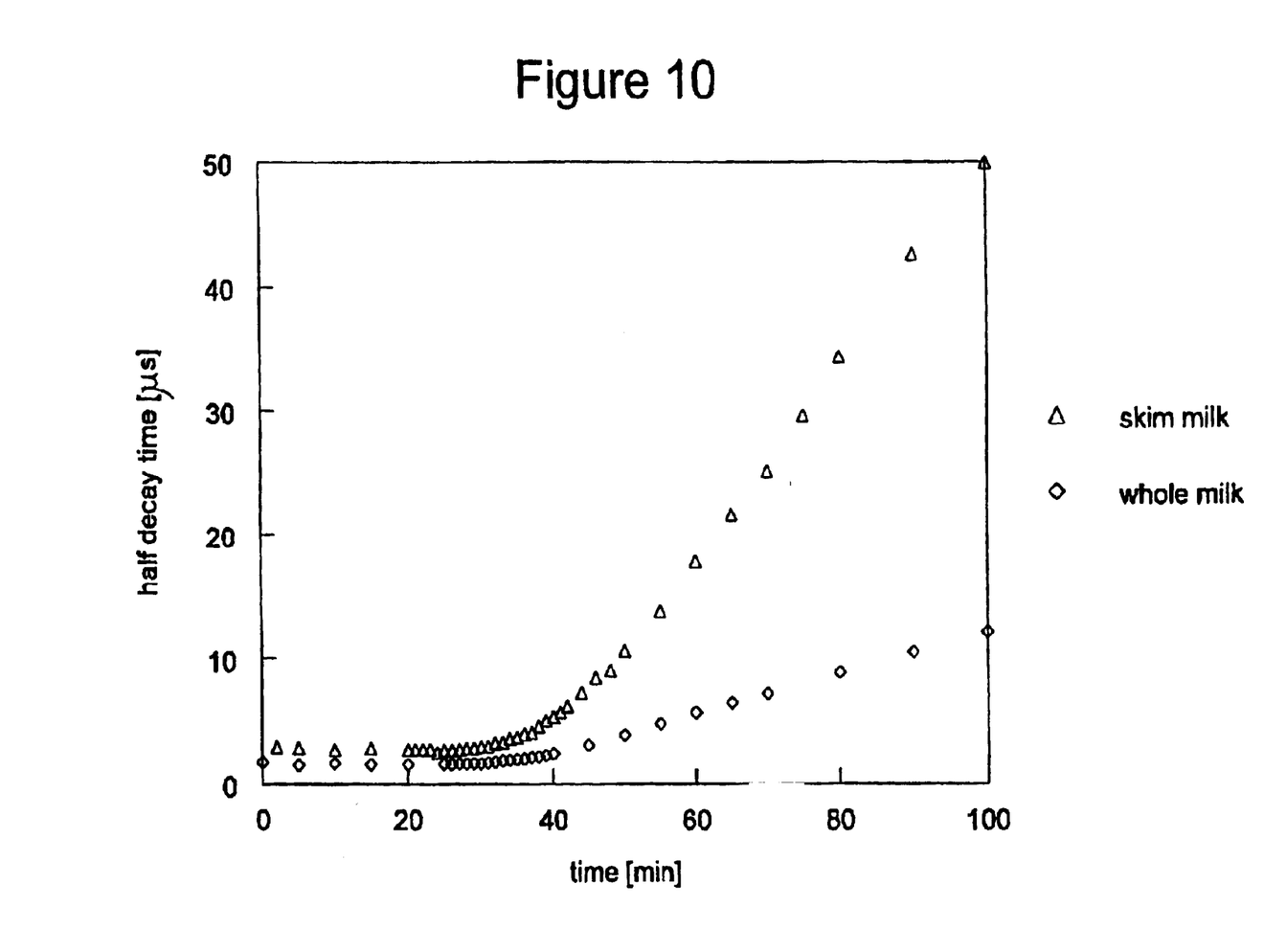
FIG. 10 compares half decay times for skim milk with those for whole milk as a function of time after that addition of rennet.

The same measurements were performed for whole milk, which has about 3.5% fat. The fat is dispersed in fat globules that contribute to the scattering of the milk. This was shown in FIG. 4. The increase in the half decay time proceeds similarly to that in skim milk (FIG. 10). Visually, it was observed that whole milk also starts to form a gel at t=40 min.

The half decay times in whole milk are smaller than those in skim milk. The half decay time increases from 1.5 μs to 25 μs. The ratio (half decay time for skim milk)/(half decay time for whole milk) increases from approximately 2 for the milks to more than 4 for the gels.

Figure 11:
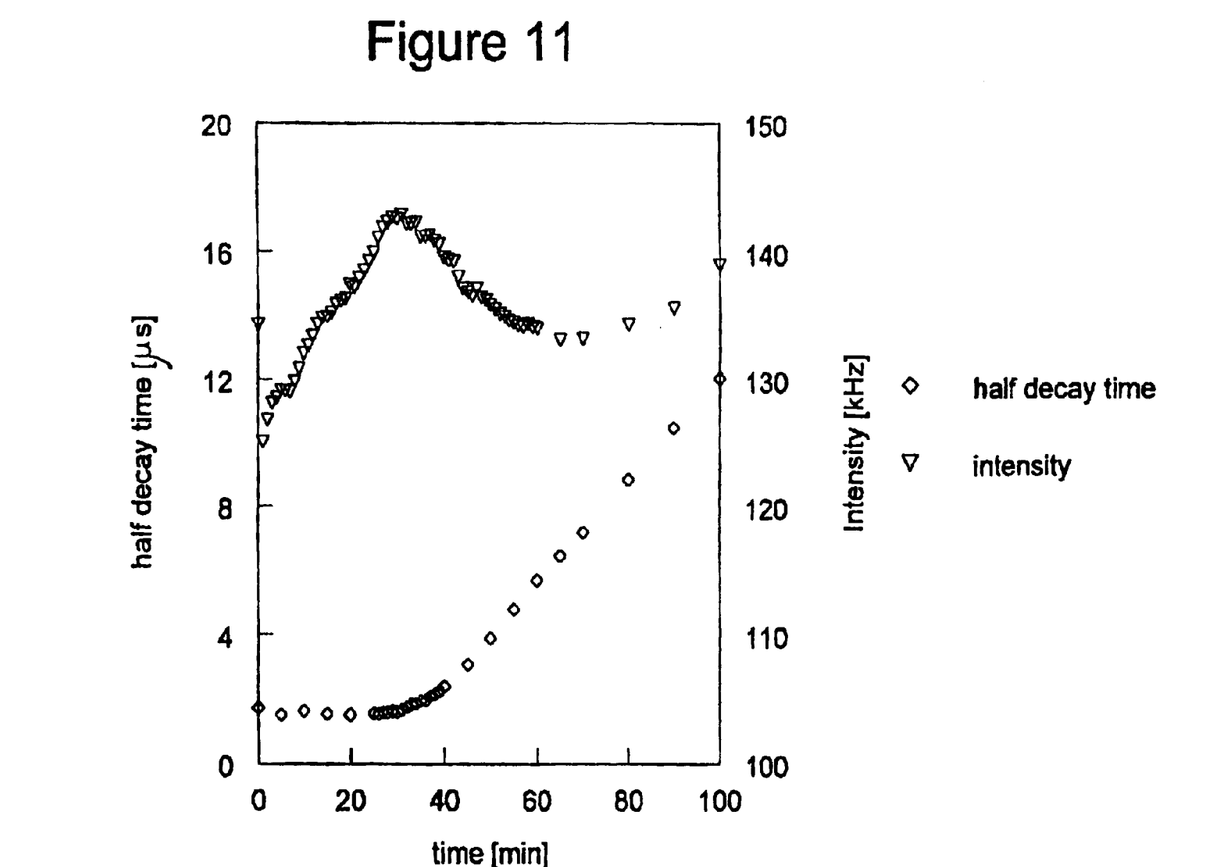
FIG. 11 compares the time dependency of the half decay time and the intensity profile for an addition of 0.02% rennet to whole milk.

FIG. 11 shows both the half decay time and intensity in whole milk after an addition of 0.02% rennet. Comparing the profiles of the half decay time and the intensity shows similar behaviour to that for skim milk.

From these measurements it can be concluded that the growth of the caseine network forming the gel is not sensitive to the addition of this amount of fat. This is very convenient for the application of DWS in cheese making.

Moreover, viscoelastic properties like gel-strength can be directly derived from the measurements made in the following way.

Gel-strength, which is given by the so-called Gelmodulus G', can be related to the mean square displacement. $<\Delta r^2>$ by making the following derivation. The principle is that a moving particle is trapped by the elasticity of the gel, which leads to a balance between the thermal energy of the particle and the strength of the gel:

$$G' \approx \frac{k_B T}{\xi \left\langle \Delta r_m^2 \right\rangle} \quad (4)$$

In this equation $k_b T$ is the thermal energy of the particle, ξ is the size of a cluster in the gel and $<\Delta r_m^2>$ is the maximum value of the mean square displacement. $<\Delta r_m^2>$ can be derived in the following way. $\Delta r^2(\tau)$ is related to the electric field correlation function $g^{(1)}(\tau)$ by equation 2. However, $g^{(1)}(\tau)$ is also a function of the time t elapsed since the addition of rennet to milk, as is for instance evident from FIGS. 5 and 6. Thus, $\Delta r^2(\tau)$ is also a function of time t. It turns out that $\Delta r^2(\tau)$ has a maximum $<\Delta r_m^2>$ for a certain τ which depends on the time t. $<\Delta r_m^2>$ is a function of time t which can be automatically monitored by means of equation 2.

The size of a gel-cluster is given by:

$$\xi = N^{1/d_f}_{cp} a \quad (5)$$

where $N_{cp}$ is the number of particles in the cluster, a is the size of particles (caseine micelles in cheese) and $d_f$ is the fractal dimension of the cluster, which is approximately 2 in a cheese-gel. The number of particles is also given by:

$$N_{cp} = \frac{N_p}{N_c} \quad (6)$$

with $N_p$ the number of particles, originally present in the milk, and $N_c$ the number of clusters in the gel. The volume fractions give another relation between a and ξ.

$$\phi_0 = \frac{N_p V_p}{V_t} \quad (7)$$

with $\phi_0$ the initial volume fraction of casein micelles in the milk (=0.1). $V_p$ the volume of a casein micelle (=4/3 Πa³) and $V_t$ the total volume of milk. The same equation can be given for the gel, which fills the whole volume, so φ~1.

$$1 = \frac{N_c V_c}{V_t} \quad (8)$$

with $V_c$ the volume of a cluster with radius ξ($V_c$=4/3Πξ³).
Combining equations 6, 7, and 8 gives:

$$N_{cp} = \frac{\phi_0 \xi^3}{a^3} \quad (9)$$

Assuming df=2 and using equation 5, this eventually leads to the following simple expression for ξ:

$$\xi = \frac{a}{\phi_0} \quad (10)$$

From equations 4 and 10 the following equation can be derived:

$$G' = \frac{\phi_0 \cdot k_B T}{a \left\langle \Delta r_m^2 \right\rangle} \quad (11)$$

In this equation a, $K_B \cdot T$ and $\phi_0$ to are constants and $<\Delta r_m^2>$ can be monitored as function of the time t. Thus, G' can be monitored as a function of the time t by processor 13. By comparing G'(t) with a reference value $G'_{ref}$ stored in memory 15 and indicating the ideal gel-strength for cutting, the cutting by cutting machine 14 can be automatically started as soon as G'(t) equals $G'_{ref}$. The memory 15 can store a table with different values for the $G'_{ref}$ for different types of milk, with different types and/or amounts of added rennet. The operator can then select the proper value of $G'_{ref}$ by means of input means 16.

Alternatively, the electric field correlation $g^{(1)}(\tau)$ can also be related to the half decay time $\tau_{1/2}(t)$. Then, by means of equation 11 the gel-strength $G'(t)$ can be expressed as a function of the half decay time $\tau_{1/2}(t)$. Thus, the processor 13 can calculate the gel-strength $G'(t)$ by measuring the half decay time $\tau_{1/2}(t)$. The advantage of this alternative method is that the half decay time $\tau_{1/2}(t)$ appears to show a rapid change of value in the area where gelation occurs and where $G'(t)$ reaches the reference value $G'_{ref}$. This latter feature results in a possibly very accurate measurement of the moment at which gelation occurs.

Furthermore, the method could even give at least an indication about the fat content of the milk that is being used by measuring the half decay time at known added percentage of rennet (of FIG. 10).

These experiments show also that to monitor the gel formation without the need to calculate the adsorption and scattering coefficients one output fibre could be used instead of 5, provided that a suitable source-detector distance is applied. This would allow the elimination of the fibre multiplexer from the experimental setup.

The laser power could be turned down to about 30 mW when the source-detector distance was 4.9 mm. Smaller distances could be used, enabling the use of lasers with even lower powers, until the distance becomes too small to ensure only multiple scattering. The DWS theory will no longer hold if the single scattering regime is reached. This will be the case if the source detector distance is in the order of the mean free path, which is about 0.4 mm in skim milk.

Above, the method according to the invention has been explained with reference to measuring/monitoring renneting of milk.

However, it can be applied in a much broader field. In particular, the invention can be applied to any system, process, medium, reaction, mixture, suspension, emulsion, etc. in which at least two phases occur simultaneously —i.e. in the same holder, vessel or reactor—and in which at least one of the phases is a liquid (phase), a fluid phase, and/or a solution.

The further phase(s) present besides said liquid phase is not particularly limited as long as it can be distinguished from said first liquid phase for the purposes of the invention, i.e. in that it influences the scattering of a laser beam that is emitted therein or therethrough.

As such, said further phase(s) can for instance be a solid phase, such as a flocculated solid phase, a suspended solid phase and/or a suspended particulate material; a semi-solid or liquid phase, which for the present purposes includes gels, aggregated states, suspended droplets of an immiscible liquid, emulsified droplets including those which occur in known W/O-emulsions, O/W-emulsions and multiple and/or inverted emulsions such as O/W/O-emulsions and W/O/W emulsions, as well as micelles; or even a gaseous phase, such as small bubbles of a suspended gas or bubbles of a gas which is led through the liquid phase. In this respect, it should be noted that in the general disclosure above, the term "particles" is used to denote any such further phase present, which is preferably distinct from the liquid phase and of small size.

The invention can be used to measure the above indicated properties of such heterogeneous systems, and in particular changes in time thereof as can occur spontaneously or —usually—as a result of a chemical reaction, a physical process or a biological process, and which lead to changes in laser beam scattering.

For instance, the system can be used to measure the stability or homogeneity of suspensions, emulsions or lattices. It can also be used to follow the course of a chemical reaction such as a polymerization, a physical process such as mixing or phase separation, or a biological conversation such as a fermentation, i.e. by following the changes in the phase(s) and/or in the interactions between them over time; or by following the changes in the composition or properties of one or more of the phases present.

Preferably, these are processes in which gel formation, coagulation, flocculation, aggregation or changes in viscosity play an important role. Also changing interactions, not necessarily leading to gelation can be measured, for example when a so-called stabilizer is added to a suspension. It might even be used to probe particles in a clear gel of e.g. polymers (Xanthan gels). Fields in which it can be applied include: fermentation, dairy (cheese, yoghurt, cream), fungi, paints, plastics and polymers, cosmetics, the oil industry, and the chemical industry.

As will be clear, the invention can also be used to study phase changes or transitions of a more homogeneous nature, or of more homogeneous (i.e. essentially single phase) systems, such as can occur in gelation, coagulation, flocculation or aggregation, or even as a result of changes in temperature. As mentioned above, for the purposes of the invention, such systems are encompassed within the term "multi-phase system", as there are differences between the initial physical state (phase) and the final physical state (phase).

The invention can also be used to measure viscosity, homogenity etc. of such systems, or changes therein over time.

The distance between the fibres falls typically in the range from 0.1 mm to 100 mm and can be adjusted. The particles are preferably in the colloidal size range, which means that their maximum size is about 10 $\mu$m.

The temperature boundaries are determined by what the optical fibres and the collimators can endure. A rough estimate is $-20°$ C.$<T<80°$ C., $2<pH<9$. About 1 measurement can be done in 5 sec with a relatively low laser power of 25 mW. When a laser with a higher power is used (e.g. 500 mW) the measuring time can be reduced to 1 sec. Changes that are slower than the measuring time can be monitored with DWS. liquid, such as solutions, dispersions and emulsions. The

What is claimed is:

1. Arrangement for measuring physico-chemical properties of liquid, such as solutions, dispersions and emulsions, comprising a light source (1) for producing and emitting light in the liquid (7), a detector for detecting said light after being scattered by said liquid (7), processing means arranged for receiving an output signal from said detector and for calculating the autocorrelation function $g^{(2)}$ of said output signal from said detector characterized in that the processing means is arranged to calculate a maximum value of the mean square displacement $<\Delta r_m^2>$ from the autocorrelation function $g^{(3)}$ as a function of time and the value of the physico-chemical property from said calculated maximum value of the mean square displacement $<\Delta r_m^2>$.

2. Arrangement according to claim 1, characterized in that the physico-chemical property is the gelstrength G', characterized in the processing means is arranged to calculate the gelstrength G' from said calculated maximum value of the mean square displacement $<\Delta r_m^2>$ using the following equation $$G' \approx \frac{k_B T}{\xi \left(\Delta r\frac{2}{m}\right)}$$

in which $k_b \cdot T$=thermal energy of particles in the gel:

$\xi$=size of a cluster in the gel.

3. Arrangement according to claim 1, comprising a machine (14) coupled to said processing means and wherein the processing means are arranged to compare said value of the physico-chemical property with a reference value of said property, and to activate the machine (14) upon the value reaching said reference value.

4. Arrangement according to claim 1, comprising a machine (14) for treating a gel, which is coupled to said processing means and wherein the processing means are arranged to compare said gelstrength G' with a reference gelstrength ($G_{ref}$), and to activate the machine (14) upon the gelstrength G' reaching said reference gelstrength for treating said gel.

5. Arrangement according to claim 1, comprising at least one detector fibre (8(1), 8(2), . . . ) arranged for detecting said light after being scattered by said liquid (7), processing means arranged for receiving an output signal from said at least one detector fibre and for calculating parameters with respect to said liquid (7) wherein any one of the at least one detector fibre (8(1), 8(2) . . . ) are located at predetermined locations with respect to each other.

6. Arrangement according to claim 5, wherein any one of the at least one detector fibre (8(1), 8(2) , . . . ) are single mode fibres.

7. Arrangement according to claim 5 wherein the source fibre (5) is a multimode fibre.

8. Arrangement according to claim 5 wherein the distances between any one of the at least one detector fibre (8(1), 8(2), . . . ) and the point of impinging of light on the liquid are larger than the mean free path of the light beam in the liquid (7).

9. Arrangement according to claim 5 wherein the light is directed to and the at least one detector fibre is immersed in a milk medium with an addition of a rennet.

10. Method according to claim 1 wherein the liquid is a milk medium with an addition of a rennet.

11. Arrangement for measuring physico-chemical properties of liquids, such as solutions, dispersions and emulsions, comprising a light source (1) for producing and emitting light in the liquid (7), a detector for detecting said light after being scattered by said liquid (7), processing means arranged for receiving an output signal from said detector and for calculating the autocorrelation function $g^{(2)}$ of said output signal from said detector, characterized in that the processing means is arranged to determine the half decay time as a function of time of the autocorrelation function and to determine the value of the physico-chemical property using a predetermined relation between the half decay time and the autocorrelation function.

12. Arrangement according to claim 1, characterized in that the physico-chemical property is the gelstrength.

13. Method for measuring physico-chemical properties of liquids such as solutions, dispersions and emulsions, comprising the steps of:
producing a light beam (2)
emitting light in a liquid (7);
detecting said light after being scattered by said liquid (7);
converting the detected light in an electrical signal;
transmitting said electrical signal to processing means;
calculating the autocorrelation function $g^{(2)}$ in the time- or the frequency domain of said electrical signal characterized in that said maximum value or the mean square displacement $<\Delta r_m^2>$ is calculated from the autocorrelation function $g^{(2)}\tau(r)$, or from $g^{(2)}(\tau)$ in a similar way, as a function of time and the value of the physico-chemical property is calculated from said calculated maximum value of the mean square displacement $<\Delta r_m^2>$.

14. Method according to claim 13, wherein the physico-chemical property is the gelstrength G', characterized in that the gel-strength G' is calculated from said calculated maximum value of the mean square displacement $<\Delta r_m^2>$ using the following equation:

$$G' \approx \frac{k_B T}{\xi \left\langle \Delta r_m^2 \right\rangle}$$

in which,
$k_b \cdot T$ = thermal energy of particles in the gel;
$\xi$ = size of a cluster in the gel.

15. Method according to claim 13, wherein the value of the physico-chemical property is compared with a reference value for controlling a machine for treating the liquid.

16. Method according to claim 13 wherein either a gelation, a flocculation or an aggregation process in the multi-phase system is monitored.

17. Method according to claim 13, comprising the steps of:
detecting said light after being scattered by said liquid (7) by means of at least one detector fibre (8(1), 8(2), . . . );
transmitting an output signal from said at least one detector fibre to processing means;
calculating parameters with respect to said liquid (7), wherein any one of the at least one detector fibre (8(1), 8(2), . . . ) are located at predetermined locations with respect to each other.

18. Method according to claim 17, wherein the distances between any one of the at least one detector fibre (8(1), 8(2), . . . ) and the point of impinging of light on the liquid are larger than the mean free path of the laser light in the liquid (7).

19. Method for measuring physico-chemical properties of liquids therein, such as solutions, dispersions and emulsions, comprising the steps of:
producing a light beam (2)
emitting light in a liquid (7);
detecting said light after being scattered by said liquid (7);
converting the detected light in an electrical signal;
transmitting said electrical signal to processing means;
calculating the autocorrelation function $g^{(2)}$ of said electrical signal, characterized in that the half decay time is calculated as a function of time or the autocorrelation function, and the value of the physico-chemical property is determined using a predetermined relation between the half decay time and the autocorrelation function.

20. Method according to claim 19, wherein the physico-chemical property is the gelstrength.

21. Method according to claim 20 wherein said gelstrength G' compared with a reference gelstrength ($G_{ref}$), and a machine (14) is activated upon the gelstrength G' reaching said reference gelstrength for treating said gel.

* * * * *